4,657,864
United States Patent [19]
Lo

[11] Patent Number: 4,657,864
[45] Date of Patent: Apr. 14, 1987

[54] METHOD FOR STABILIZING PEROXIDASE SOLUTIONS

[75] Inventor: David K. Lo, Silver Spring, Md.

[73] Assignee: Westvaco Corporation, New York, N.Y.

[21] Appl. No.: 745,953

[22] Filed: Jun. 18, 1985

[51] Int. Cl.$^4$ ............................ C12N 9/08; C12Q 1/28
[52] U.S. Cl. ...................................... 435/192; 435/28; 435/814
[58] Field of Search ................... 435/192, 188, 28, 814

[56] References Cited

U.S. PATENT DOCUMENTS 3,947,324  3/1976  Lakshminarayann .......... 435/814 X

Primary Examiner—Lionel M. Shapiro

[57] ABSTRACT

Solutions containing peroxidase enzymes may be treated to increase their stability and shelf life by reducing their protease level and filtering through a microporous filter to remove any microbial contamination that might secrete additional protease enzymes.

2 Claims, No Drawings

METHOD FOR STABILIZING PEROXIDASE SOLUTIONS

BACKGROUND OF INVENTION

The present invention relates generally to the preparation and storage of the enzyme peroxidase, and more particularly to a method for treating a solution containing peroxidase enzyme to increase its stability and shelf life.

Peroxidase enzymes are fairly ubiquitous, occurring in higher plants, yeasts, molds, bacteria and mammals. The enzyme peroxidase, especially horseradish peroxidase, has many uses. Of particular importance is its use in reagents employed in immunoassays. Horseradish peroxidase has also recently been found to be useful in a biocide formulation. In the latter use, the enzyme is relied on for its ability to catalyze the oxidation of phenolic materials, (see U.S. Pat. No. 4,370,199 and U.S. Pat. No. 4,478,683, assigned to the present assignee). Nevertheless, the major obstacle to the widespread use of peroxidase enzymes particularly for industrial applications is that their desired qualities ae not maintainable over any substantial period of time when stored in low concentration either in the dissolved or suspended states. Microbial contamination appears to be the major contributing factor for the instability of peroxidase enzymes, however, peroxidase activity may also decrease during, or as a result of the manner in which they are stored. It is known that peroxidases are not very stable for long term storage at high tempertures (e.g. above 25 degrees C.) especially in solution. As a result, samples of peroxidase have to be stored in a cold condition (e.g. 4 degrees C. or less) and preferably in the solid state.

U.S. Pat. No. 4,169,012 and No. 4,228,240 each describe methods for stabilizing peroxidase compositions by adding polyvalent ions of Groups III and IV of the Periodic Table to reagents containing peroxidase compositions. U.S. Pat. No. 4,252,896 discloses a method of stabilizing peroxidase in a serum protein based medium with the addition of a stabilizingly effective amount of 8-anilino-1-naphthlenesulfonic acid (ANS). According to this method, the amount of activity remaining after 43 days storage at 45 degrees C. is about 43%. Finally, U.S. Pat. No. 4,448,882 discloses a method of stabilizing a peroxidase composition in a serum protein with the addition of a stabilizing amount of 4-amino-antipyrine (AAT). According to this method about 58% activity remains after 28 days storage at 37 degrees C.

In contrast to the above prior art, the present invention relates to a method for the stabilization of a peroxidase containing solution without the use of additives or stabilizers. Moreover, the method of the present invention produces a peroxidase composition that can be stored substantially indefinitely at room temperature. As a result, the present invention differs from U.S. Pat. No. 4,169,012 and U.S. Pat. No. 4,228,240 which require the addition of a polyvalent ion and storage in the freeze dried state, and from U.S. Pat. No. 4,252,896 and U.S. Pat. No. 4,448,882 which require the addition of stabilizing agents and storage at an elevated temperature.

SUMMARY OF INVENTION

It has surprisingly now been found that the stability of a peroxidase solution can be maintained by preparing a sterile aqueous solution which is devoid of proteolytic activity. Essentially the method disclosed herein comprises selecting a peroxidase solution of low protease content, or treating the peroxidase solution to reduce its protease content, and then filtering the solution through a microporous membrane to sterilize and remove from the solution any microbial contamination that might secrete additional protease enzyme.

Protease enzymes (proteolytic enzymes) are a class of enzymes which hydrolyze proteins to amino acids and polypeptides (proteinases). Thus, proteases are water soluble products which degrade proteins. Since the enzyme peroxidase is also a protein, obviously proteases can degrade peroxidase. The protease activity of a peroxidase enzyme can be correlated with the stability of the enzyme.

Microbial contamination also plays a role in the stability of peroxidase enzymes. Microorganisms secrete proteases which can further contaminate and degrade the enzyme. Thus, a peroxidase enzyme solution which is devoid or even low in proteolytic activity (reduced protease activity), may still be rendered unstable unless it is also sterilized or placed in a sterile environment to reduce microbial degradation. Simply sterilizing a peroxidase solution without regard to its protease level will not insure a shelf-stable product.

Further, merely choosing an enzyme with a low protease level or treating an enzyme to reduce its protease level will also not insure a shelf-stable product. However by selecting an enzyme solution having a low protease level, or by treating a solution to reduce its protease level prior to sterilization, one can achieve a shelf-stable product with reliable residual activity. Solutions of horseradish peroxidase having low protease activity are available from Sigma Chemical Company, St. Louis, Mo., or from Bio Conn Company, Louisville, Ky. However, where desired, the protease activity of a peroxidase solution can be effectively reduced by heating the solution at 56 to 85 degrees C., preferably 60 degrees C., for 5 to 30 min., and then cooling the solution to a temperature of 0 to 4 degrees C.

DETAILED DESCRIPTION

The present invention relates to a method for increasing the stability and shelf life of peroxidase enzymes, and more particularly to a method for stabilizing the activity of solutions of horeseradish peroxidase.

EXAMPLE

Four enzyme samples were selected for study having different levels of protease contamination and enzyme activity. Enzyme activity is specified in purpurogallin units (PPGU), and the specific activity of each enzyme is defined in PPGU/mg of enzyme. The specific activity of the samples selected ranged from about 4 PPGU/mg to about 240 PPGU/mg. Protease activity is specified in units per milligram of the enzyme (U/mg). Protease enzyme activity is measured by the casein digestion assay using *Staphylococcus aureus* protease as a reference standard. One unit of protease liberates 0.001 $A_{280}$ acid soluble fragments from casein/minute at pH 7.8 and 37 degrees C. The protease activity of the samples selected ranged from about 0.026 U/mg to 2.65 U/mg.

Solutions of these enzyme samples were prepared to a concentration of about 0.6–0.8 PPGU/ml in 0.1M phosphate buffer at a pH of 6.0. All but one of the solutions were then sterilized by filtration through a 0.22 $\mu$m filter and divided into aliquots of 5 ml. These aliquots were stored in sterile vials at 25 degrees C. From time to time the vials were assayed for peroxidase activity using the standard Sigma assay. The Sigma assay comprised an assay medium consisting of 10.7 mM phosphate buffer at pH 6.0; 7.8 mM hydrogen peroxide; 0.53% (w/v) pyrogallol; and, 100 µl of the sterilized peroxidase solution. Enzyme activity was determined spectrophotometrically by measuring the change in absorbance at 420 nm and 20 degrees C. at 20 second intervals for 3 minutes. The residual activity was determined by calculating the percent enzyme activity remaining at the designated time intervals. The following Table illustrates the results of the study.

TABLE

| Sample | Enzyme Activity (PPGU/mg) | Protease Level (U/mg) | Residual Activity Days (%) | | | | | |
|---|---|---|---|---|---|---|---|---|
| | | | 7 | 14 | 34 | 43 | 63 | 160 |
| A | 4.04 | 0.026 | — | — | 98 | — | 100 | 109 |
| B | 241.15 | 0.325 | — | — | 96 | — | 96 | 104 |
| C | 44.93 | 0.487 | 92 | 105 | — | 101 | — | — |
| D | 13.2 | 2.65 | 21 | 12 | — | 11 | — | — |
| E* | 241.15 | 0.325 | 80 | 53 | 53 | — | 36 | — |

*Sample E was not filtered.

The study results showed that for a peroxidase solution having a protease level less than about 0.5 U/mg (samples A, B and C), the method of the invention produced a substantially stabilized product where the % residual enzyme activity remained substantially unchanged for a period of nearly 6 months. This conclusion was reinforced by the performance of Sample E, which was in all respects the same as B except for being unfiltered. Sample E showed a continued decline in residual activity through day 63.

For the purpose of the present invention, the peroxidase enzyme solution may have an initial protease level ranging from about 0.02 to about 0.5 U/mg dry weight, but is preferably no greater than about 0.3 U/mg. The filter element for the sterilization step may have a pore size in the range of from about 0.20 to 0.45 µm, but is preferably no greater than about 0.22 µm. Meanwhile, the sterilized solution may be stored at a temperature of between about 10–30 degrees C., but should be no greater than about 30 degrees C.

What is claimed is:

1. Process for the stabilization of peroxidase containing solutions comprising:
   (a) preparing a peroxidase solution to achieve a protease activity of from about 0.02 to 0.5 U/mg dry weight;
   (b) filtering the solution through a membrane having a pore size in the range of from about 0.20 to 0.45 µm to produce a sterilized solution; and,
   (c) storing the sterilized solution in sterile containers at a temperature of between about 10–30 degrees C.

2. Process for the stabilization of peroxidase containing solutions comprising:
   (a) treating a peroxidase solution to achieve a protease level less than about 0.5 U/mg dry weight;
   (b) filtering the treated solution through a membrane having a pore size of about 0.22 µm to produce a sterilized solution; and,
   (c) storing the sterilized and treated solution in a sterile container at a temperature of about 25 degrees C.

* * * * *